United States Patent [19]

van der Veen

[11] Patent Number: 5,522,858
[45] Date of Patent: Jun. 4, 1996

[54] PACEMAKER WITH IMPROVED REACTION TO STABLE FIRST DEGREE ATRIO-VENTRICULAR BLOCK

[75] Inventor: Johannes S. van der Veen, Dieren, Netherlands

[73] Assignee: Vitatron Medical, B.V., Dieren, Netherlands

[21] Appl. No.: 329,291

[22] Filed: Oct. 26, 1994

[51] Int. Cl.$^6$ .................................................. A61N 1/36
[52] U.S. Cl. .................................................. 607/14
[58] Field of Search .................................. 607/9, 14, 25

[56] References Cited

U.S. PATENT DOCUMENTS

| | | |
|---|---|---|
| 4,467,810 | 8/1984 | Vollmann . |
| 4,562,841 | 1/1986 | Brockway et al. . |
| 4,967,746 | 11/1990 | Vandegriff .................... 607/9 |
| 5,247,930 | 9/1993 | Begemann et al. ............ 607/11 |
| 5,269,299 | 12/1993 | Duncan ........................ 607/9 |
| 5,273,035 | 12/1993 | Markowitz et al. ............ 607/14 |

OTHER PUBLICATIONS van Gelder, Barry M. et al., "Apparent P Wave Undersensing in a DDD Pacemaker Post Exercise," PACE, vol. 15, Nov., Part I 1992, pp. 1651–1656.

Fearnot, Neal E., "A Review of Pacemakers That Physiologically Increase Rate: The DDD And Rate-Responsive Pacemakers," Progress in Cardiovascular Diseases, vol. XXIX, No. 2 (Sep./Oct. 1986), pp. 145–164.

Primary Examiner—William E. Kamm
Assistant Examiner—Jeffrey R. Jastrzab
Attorney, Agent, or Firm—Woodcock Washburn Kurtz Mackiewicz & Norris

[57] ABSTRACT

A dual chamber cardiac pacemaker system has logic for detecting high rate as well as normal atrial spontaneous signals, and for tracking atrial signals within a predetermined tracking rate range by delivering ventricular pace pulses at an AV interval following each atrial sense within said tracking range. The pacemaker also has detection circuitry for detecting a sequence of pacemaker cycles characterized by first degree AV block, wherein atrial sense signals occur too early to permit tracking, and ventricular spontaneous signals occur following an extended AV-delay such as is characterized by first degree block. The pacemaker restores tracking following detection of such a sequence by delivering ventricular pace pulses at an extended AV interval to override the spontaneous ventricle signals and gradually decreasing the AV-delay back to a normal value, thereby restoring tracking without pacing the ventricle at an excessive rate.

18 Claims, 4 Drawing Sheets

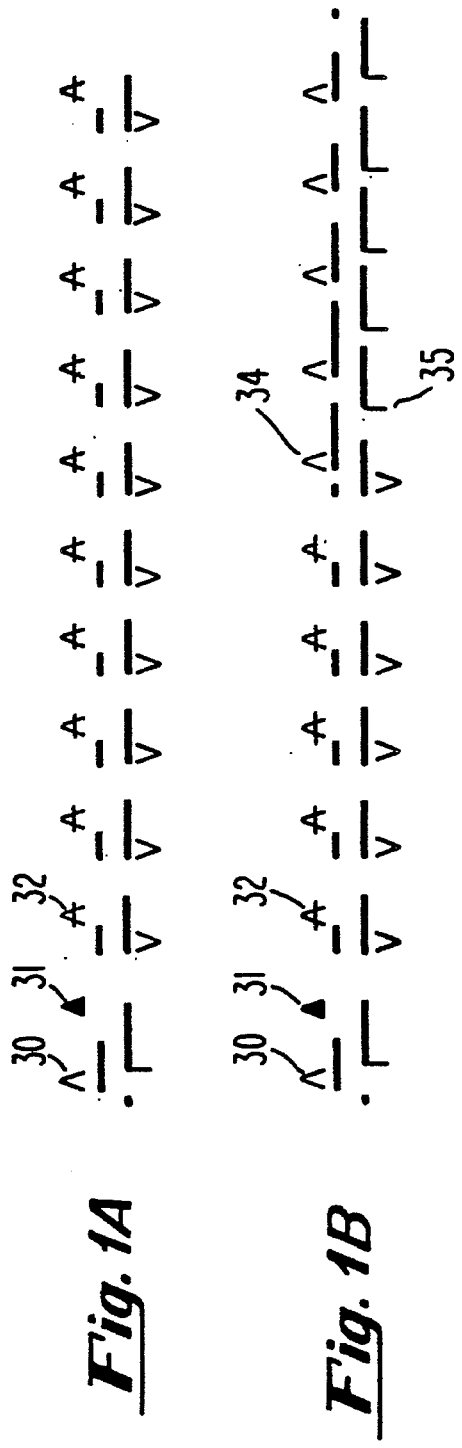
Fig. 1A
Fig. 1B
Fig. 4
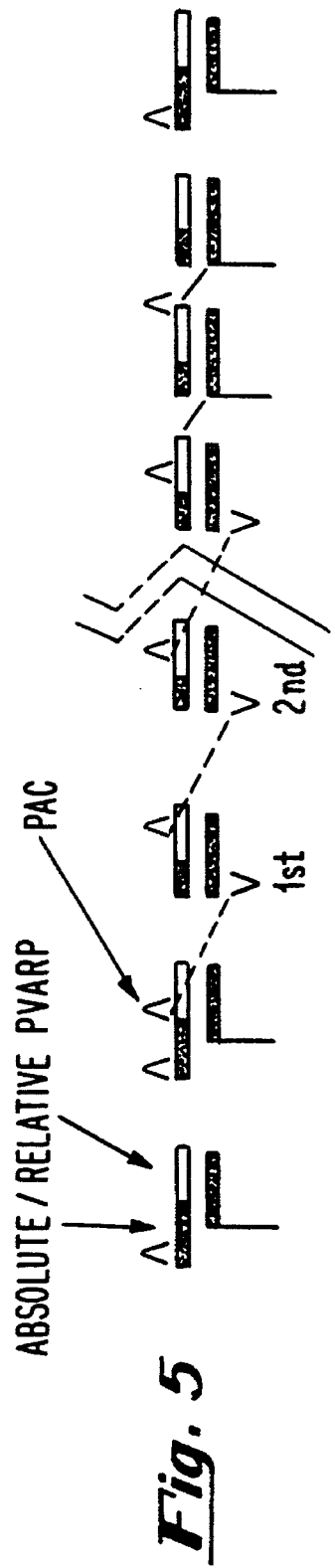
Fig. 5

PACEMAKER WITH IMPROVED REACTION TO STABLE FIRST DEGREE ATRIO-VENTRICULAR BLOCK

BACKGROUND OF THE INVENTION

The present invention relates to dual chamber pacemakers and, more particularly, dual chamber pacemakers which maximize the recognition of early atrial senses so as to detect tachycardia.

Tachycardia detection has assumed a role of high importance in design of modern dual chamber pacemakers. The ability to detect tachycardia episodes, collect data concerning such episodes which can be outputted to the physician, and to provide remedial responses where appropriate, has been the object of considerable design effort in the pacemaker area. The approach taken by Vitatron Medical, B. V., the assignee of this invention, has involved minimizing the atrial no-sense period (ANSP), so that most spontaneous early atrial events can be sensed. Thus, if theoretically no blanking period were ever used following an atrial sense, the pacemaker would be capable of collecting the maximum amount of information concerning early atrial senses, and thus would be in the best possible position to determine the onset of atrial tachycardia. Of course, such a pacemaker would have to have sophisticated logic to determine when and how such early atrial senses can be used.

Our investigations have shown that such a pacemaker with an advanced arrhythmia detection capability can react poorly to stable first degree AV block ("AVB1"), under circumstances where an early atrial sense, such as a premature atrial contraction (PAC), is followed by a lengthened spontaneous AV conduction duration. In this situation, the pacemaker may be "trapped" in a situation initiated by the lengthened AV conduction duration where a next following atrial signal is sensed but arrives too early to permit the pacemaker to follow with a tracked ventricular pulse. Such an early atrial sense cannot be tracked because the ventricular pace pulse would be delivered at too short an interval compared with the prior ventricular event, i.e., it would correspond to an excessive ventricular rate. In a pacemaker such as described in U.S. Pat. No. 5,247,930, assigned to the assignee of this invention and incorporated herein by reference, there is established a dynamic tracking limit (DTL), and a condition for tracking an atrial sense is that the resulting ventricular rate cannot exceed DTL. Further, the AV interval cannot routinely be extended past a predetermined maximum, in order to prevent pacemaker mediated tachycardia (PMT). Thus, the combination of sensing high rate early atrial spontaneous beats, together with the built-in logic of controlling when the atrial event can and cannot be sensed, can lead to a problem when applied to patients with first degree AV block, namely that the pacemaker is "trapped" or "stuck" in a situation where atrial paces are not delivered since the spontaneous P-wave is seen, and ventricular paces are not delivered because this would result in an excessive ventricular rate. The result is that a single PAC, or incidental undersensing such as sometimes occurs in a VDD, can initiate a prolonged period of time during which the patient is suffering first degree block and the pacemaker does not intervene.

AVB1 can also occur in a conventional pacemaker which responds to a PVC by extending PVARP. In such pacemaker, after a PAC which occurs in the PVARP, and is not tracked, there can be a VS before timeout of the escape interval, which is seen as a PVC. When PVARP has been extended, the subsequent AS which reoccurs at a constant rate is blocked, resulting in another VS after a lengthened AV-delay, and so on. In this case also, it is seen that there is good reason to minimize the atrial blanking period so as to detect AVB1, and react quickly and actively. See also the paper titled "Apparent P-Wave Undersensing In A DDD Pacemaker Post-Exercise," van Gelder et al., *PACE*, Vol. 15, November 1992, Part I, pp. 1651–1656.

The above-noted problem which can arise in a patient with first degree AV block, and who has a pacemaker with a minimal ANSP, is illustrated in the timing diagram of FIG. 1A. In FIG. 1A, as well as the timing diagrams of FIG. 1B and FIG. 4, the following symbols and abbreviations are used:

| SYMBOL | DESCRIPTION | ABBREVIATION |
|---|---|---|
| ∧ | Normal Atrial Sense | NAS |
| ∨ | Normal Ventricular Sense; a VS with a V-V interval within the rate limits, which is preceded by an A_Event. | NVS |
| ▲ | Premature Atrial Contraction | PAC |
|  | Normal Atrial Sense that is blocked, i.e., cannot be tracked because it is too early; tracking would result in too short a V-V interval. | NAB |
|  | AV-delay | AV |
|  | AV Extension | AV Ext |
|  | Wenckebach | WB |
|  | Dynamic Tracking Limit (highest rate at which pacemaker will track atrial senses) | DTL |
|  | Interval corresponding to DTL | DTL_int |
| ▬ | Blanking Period-atrial or ventricular |  |
| ▐▀ | Stimulus Pulse (followed by blanking period) | VP |

In the timing diagram of FIG. 1A, the natural sinus rate is represented as being steady at 120 bpm. The patient has a lengthened spontaneous AV conduction of 350 ms. A first atrial sense 30 is tracked by delivery of a ventricular pulse, following a normal AV-delay. Then, a single PAC 31 occurs. Following the PAC, which is not tracked, the spontaneous AV conduction takes 350 ms, resulting in a ventricular sense. Following this, and following a short ANSP, a next spontaneous atrial signal is sensed at 32. This signal is seen, but tracking is blocked, since a tracked ventricular pulse, even at a maximum AV-delay, would follow too closely to the prior spontaneous ventricular signal. For this reason, this atrial sense is referred to as a normal atrial blocked signal, or NAB. While the pacemaker is waiting for the V—V escape interval to time out, the spontaneous AV conduction period expires and the pacemaker sees a normal ventricular sense (NVS). This process is illustrated as being repeated indefinitely, the pacemaker being unable to escape the situation in which it is locked due to the single PAC and the first degree AV block which results in a lengthened spontaneous conduction. Thus, each cycle the A-sense is too early to track, following too shortly after the V-sense; there then follows a lengthened spontaneous AV conduction, resulting in a next A-sense which again is too early to track. The pacemaker can stay in this NAB-NVS situation for an indefinite period. Further, this problem can be more likely to occur when the upper tracking limit is dynamic, as in the pacer of the above-referenced U.S. Pat. No. 5,247,930. This is because the dynamic tracking limit, or DTL, could drop to a lower value, e.g., 100 ppm, increasing the probability of an A-sense coming too early to track, and thus being treated as an NAB.

It is thus seen that there is a need for a pacemaker having an improved capacity to detect an inadequate response to first degree AV block, or a similar condition other than total AV block. If, for any combination of the patient condition and the pacemaker logic, the pacemaker can fall into a situation where the natural heart function is unsatisfactory and the pacemaker does not take over and pace, there must be provided a way to detect the situation and enable the pacemaker to resume optimal pacing. For a DDD or VDD pacemaker, it is, of course, desirable to resume atrial tracking as quickly as possible.

SUMMARY OF THE INVENTION

It is an object of this invention to provide a dual chamber pacemaker having maximized sensing of atrial signals, and having an improved capability of maintaining atrial tracking during spontaneous atrial anomalies. Such anomalies may include stable first degree atrio-ventricular block and intermittent atrio-ventricular block, first degree or otherwise.

In accordance with the above object, there is provided a pacemaker of a design having a minimized ANSP so as to enable detection of as many atrial signals as possible, including spontaneous atrial events which may be classified as atrial tachycardia. The pacemaker is further provided with the capability of recognizing and determining when the pacemaker is not providing atrial tracking under circumstances where such tracking is desired, such as can be caused by first degree AV block. This object is carried out by recognizing, by application of predetermined criteria, a sequence of spontaneous atrial signals (P-waves) each followed by a spontaneous ventricular signal under circumstances where the pacemaker should normally deliver ventricular pace pulses in a tracked relation to the sensed P-waves. When such a sequence is recognized, the pacemaker intervenes and delivers ventricular pace pulses at a temporarily lengthened AV interval from the sensed P-waves, decreasing the AV interval at succeeding cycles until the pacemaker regains normal tracking of the spontaneous atrial signals.

BRIEF DESCRIPTION OF THE DRAWINGS

FIG. 1A is a timing diagram showing an illustrative example of a condition where the pacemaker does not track sensed P-waves, and the patient is in first degree AV block. FIG. 1B is a timing diagram which illustrates the same underlying spontaneous cardiac condition, where the pacemaker is improved so that it recognizes the problem that has occurred and intervenes to restore normal atrial tracking.

FIG. 4 is a timing diagram illustrating the operation of the invention in a situation where the failure to track in a patient with first degree AV block is intermittent.

FIG. 5 is a timing diagram illustrating the operation of this invention in a pacemaker having an absolute PVARP blanking period and a relative PVARP, showing how detection of n out of N cycles having an AS in the relative PVARP followed by a VS after an extended AV interval, is diagnosed as AVB1 and followed by an appropriate pacemaker response.

DESCRIPTION OF THE PREFERRED EMBODIMENTS

Figure 2:
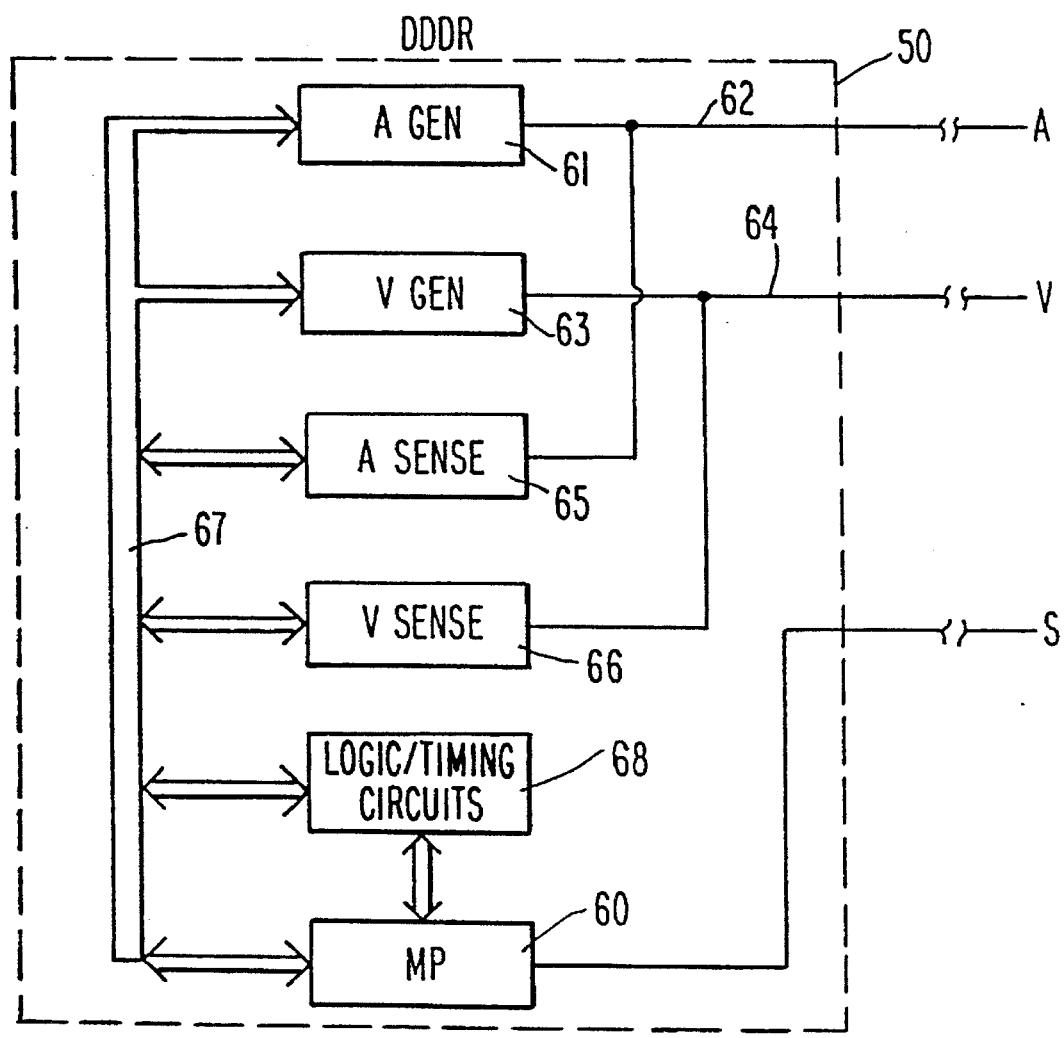
FIG. 2 is a block diagram of a typical dual chamber cardiac pacemaker system, showing the primary component blocks of the system.

Referring now to FIG. 2, there is shown a basic block diagram of the primary hardware components of a DDDR pacemaker 50. An atrial generator 61 is shown, having an output connected to lead 62 which communicates with the patient's atrium. An A-sense amplifier 65 is illustrated also connected to atrial lead 62. A ventricular generator is illustrated which is connected to the patient's ventricle through lead 64. V-sense amplifier 66 is also connected to lead 64, to receive and sense signals from the patient's ventricle. Generators 61 and 63 and sense blocks 65 and 66 are interconnected with microprocessor system 60, which microprocessor has software which is parameter-driven to control the operation of the hardware units. Microprocessor system 60 may be interconnected with hardware logic and/or timing circuits 68. The microprocessor system suitably consists of a microprocessor with appropriate ROM and RAM; and may include a separate memory chip with ROM and RAM. It is preferred that the operating software fit in ROM and have available sufficient bytes of RAM. A certain amount of RAM capacity is held unused to enable future RAM routines (executable code located in RAM). In a manner well known in the art, the software contains a number of strategic places where escape points to a RAM routine are available. As affects the scope of this invention, the degree to which software supplants hardware, or vice versa, is a matter of design choice. Thus, for the many timing functions that are carried out in the pacing system of this invention, it is to be understood that the microprocessor may have built in timing circuits, or suitably may control external hardware timer circuits. Software control of pacing function is well known in the art, such that the following detailed discussions of the software specifications enable one of ordinary skill in this art area to design a system for carrying out the functions within the scope of the invention. Data inputted from an external programmer is stored in memory associated with microprocessor. FIG. 2 also shows a sensor S, indicated as providing an input to microprocessor system 60, for providing rate parameter data to be used in a DDDR processor.

Referring now to FIG. 1B, the timing diagram that is presented illustrates the technique of recognizing and departing from the repeating NAB-NVS sequence in which a pacemaker can find itself locked. Comparing FIG. 1B with FIG. 1A, the atrial sequence 30, 31, 32 is the same, namely a normal atrial sense (NAS) followed by a PAC, followed by an atrial sense that is blocked (NAB). As illustrated in FIG. 1B, there are five consecutive NAB-NVS pairs, and these are counted by the pacemaker. While different criteria for determining when tracking needs to be restored are set forth below, for purposes of illustration in FIG. 1B it is assumed that the pacemaker looks for five consecutive such NAB-NVS pairs. If such are found, the pacemaker then recognizes each following P-wave and tracks it by delivering a ventricular pace pulse at an extended AV interval. Thus, the interval between P-wave 34 and ventricular pace 35 is greater than normal maximum allowed AV interval, but less than the spontaneous AV conduction time. Each successive P-wave is tracked with an AV interval which is decremented each cycle until the AV-delay is brought within a normal limit, and normal tracking is resumed. By way of example, if the spontaneous AV is 350 ms, and the normally allowable maximum extended AV-delay is 165 ms, the AV-delay at 35 can start at 340 ms, and be decremented each succeeding cycle by 25 ms until it is within the limit of 165 ms. In this way, normal tracking can be reestablished within a small number of cycles, without pushing the ventricular pace rate above the upper tracking limit (UTL).

The existence of a sequence of NAB-NVS pairs, such that tracking must be restored, is used to define the occurrence of AVB1. The determination of AVB1 may follow the simple procedure of counting consecutive NAB-NVS pairs, or may use more complex criteria. However, it is preferred that NAB-VP sequences are not counted, since a number of such sequences probably are due to retrograde conduction, and tracking these NABs would lead to pacemaker-mediated tachycardia (PMT). Likewise, NAB-TVS (TVS is tachy ventricular sense) pairs are not counted, to avoid detecting a V tachy with retro-A-senses (e.g., 2:1 retro-conduction). Further, our tests have indicated that in some borderline cases, some early A-senses may be tracked, and others may not be. The behavior of the pacemaker may vary for only slight sinus-rate (atrial rate) variations. The pacemaker should be able to detect AVB1 even though NAB-NVS pairs are not successive, and thus preferably uses a detection algorithm which reliably detects when NAB-NVS pairs occur in a pattern that meets predetermined criteria. In the illustrative algorithm presented, the NAB-NVS pairs are counted, but do not have to reach a certain count without interruption. The number counted needs to be low, to provide quick detection; but should be high enough to avoid false detection of AVB1 in the case of a few ventricular early senses with retro-A-senses. A preferred trade off yields a count of 5. Similarly, the number of cycles with a long AV-delay after detection of AVB1 must be high enough to enable restoration of tracking with normal AV-delays. And it must be low enough to prevent PMT's if some ventricular early senses with retro-A-senses occur during the restoration with long AV-delays. An appropriate number of cycles is 10.

Figure 3A:
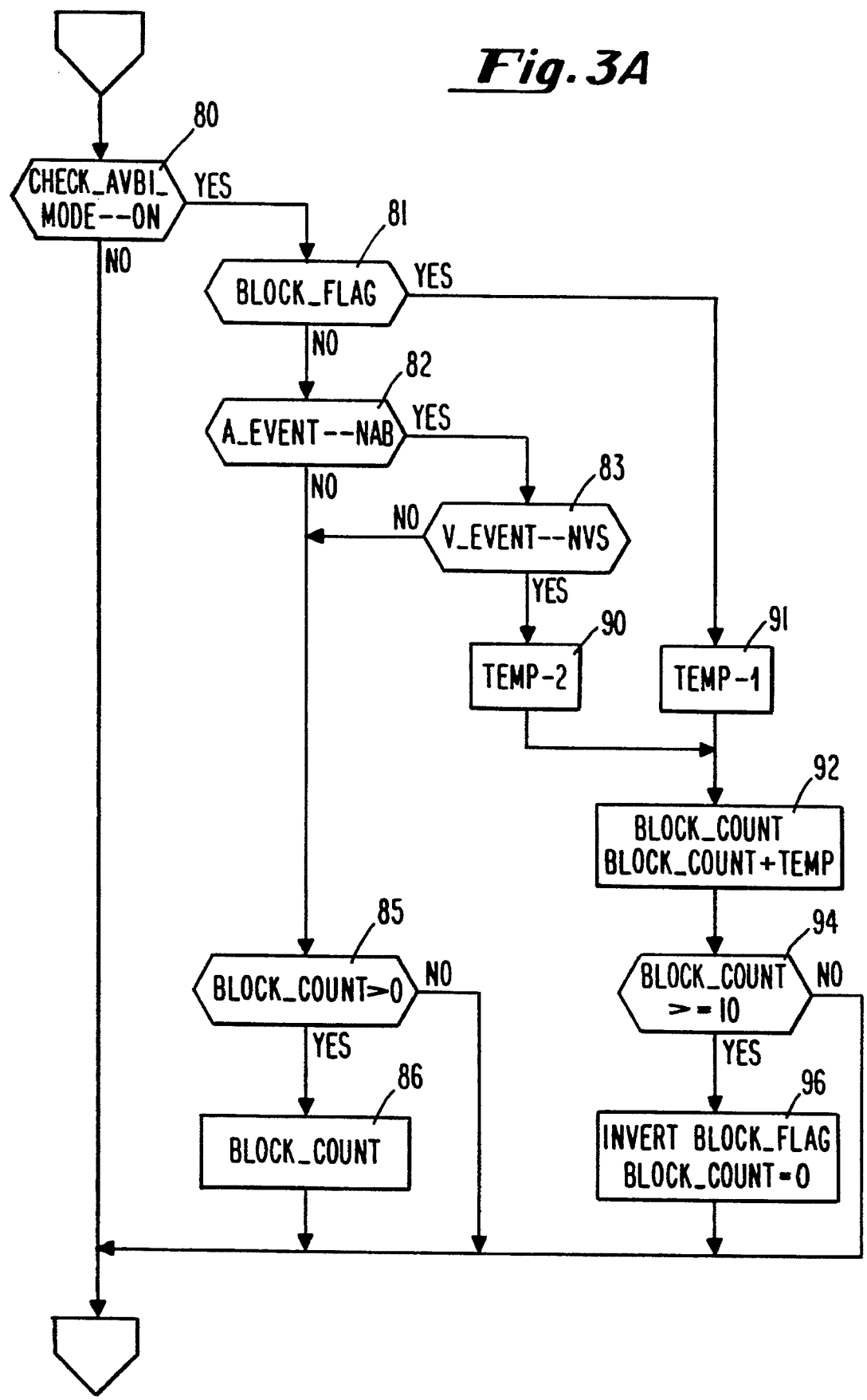
FIG. 3A is a flow diagram illustrating the steps carried out by the pacemaker of this invention for detecting a sequence where the pacemaker is failing to track sensed P-waves of a patient with first degree AV block, and of the steps carried out by the pacemaker of this invention for controlling the sequence for restoring normal atrial tracking following detection of a tracking failure.

Referring now to FIG. 3A, there is shown an illustrative flow diagram for the logic carried out by the pacemaker of this invention in determining when the criteria for NAB-NVS sequences is met, and for counting out the following cycles of lengthened AV-delay during which the pacemaker reestablishes normal tracking. The routine is entered at 80, where it is determined whether the pacemaker is programmed to search for the non-tracking sequence that can result from AV first degree block, i.e., whether the pacemaker is in the "AVB1" mode. If yes, the pacemaker at 81 determines whether the "block" flag is set. The block flag, which is controlled at 94, is set when a sequence has been found, e.g., when five NAB-NVS pairs have been detected. If the block flag is not set, meaning that the pacemaker is monitoring for the non-tracking AVB1 condition, the routine branches to 82 and determines whether the most recent A event is an NAB. If it has been, the routine goes to block 83 and determines whether the V event was an NVS. If yes, a factor termed "temp" is set equal to 2, and the routine goes to block 92 where the block count is incremented by the value of temp. At 94, the block count is compared to see if it has reached 10, and if yes, at 96 the routine inverts the block flag and sets the block count equal to zero. Thus, the block count is increased by 2 for each NAB-NVS pair, such that five such pairs cause the block flag to be set. As seen, until the block count is found to be 10, the program branches from 94 and exits. Note that a count of 10 corresponds to 5 NAB-NVS pairs. Returning to block 82, if the A event is determined not to be an NAB, the program goes to block 85, and determines whether the block count is greater than zero. If it is not greater than zero, the routine simply exits. If it is greater than zero, the block count is decremented by 1. Note that occasional NAB-NVS pairs, e.g., one per day, cannot be accumulated, and decrementing prevents this. Thus, the pacemaker does not have to find consecutive NAB-NVS pairs, (such as illustrated in FIG. 1B) but can still reach a block count of 10 or greater even though there are intermittent tracking cycles. Likewise, if the A event is an NAB, but at 83 it is determined that the V event is not an NVS, the routine branches to 85.

Returning to block 81, if the block flag is set, meaning that AVB1 has been detected, the routine branches to block 91, where the factor "temp" is set equal to 1. Then, at 92, the block count is incremented by only 1, following which the block count is compared to 10 at 94. By setting the temp factor equal to 1 when the block flag is set, the pacemaker has 10 cycles during which the V—V interval is shortened by a predetermined amount.

Figure 3B:
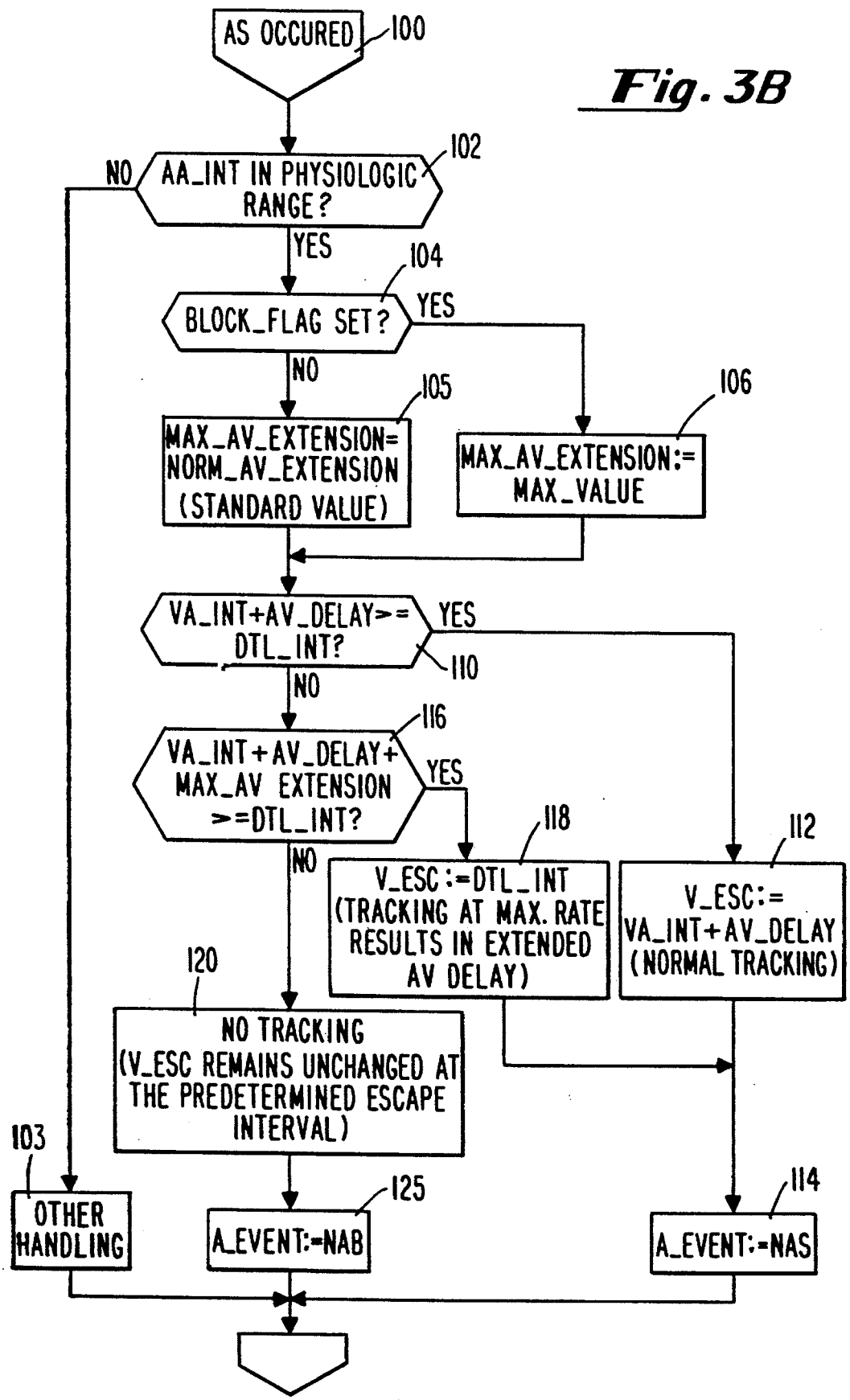
FIG. 3B is a flow diagram showing the tracking routine of the pacemaker of this invention which results in restoring tracking after a sequence of non-tracking due to AVB1.

Referring now to FIG. 3B, there is illustrated a subroutine for responding to detection of AVB1 by pacing with longer AV intervals. As seen in this routine, the algorithm does not set the AV extension as such each cycle. Rather, the pacemaker uses a maximum value of AV extension and determines then whether the V—V pacing rate would be less than the dynamic tracking limit and, if so, paces at the dynamic tracking limit. When this is done, the V rate accelerates relative to the A rate, such that the ventricular pulses effectively catch up with the early A-senses, so that normal tracking can be resumed. This action is seen in an examination of the details of FIG. 3B.

Referring to FIG. 3B, at 100 it is determined that an atrial sense has occurred. At 102 it is determined whether the A—A interval is in the physiological range, i.e., is it a candidate to be tracked with a synchronous ventricular pulse? If no, the routine exits to 103, for other handling that is not relevant to this arrangement for responding to AVB1. If the A—A interval is physiologic, the routine proceeds to block 104, and determines whether the block flag has been set. If no, then the value for the maximum AV extension is set equal to the normal value of the AV extension. However, if the block flag has been set, meaning that AVB1 has been detected, the routine branches to 106 and sets the maximum AV extension equal to its maximum value. A representative value for Max_AV_extension is 210 ms.

At block 110, the pacemaker adds the value of the VA_int+AV_delay, and compares to DTL_int. If the combined value is equal to or greater than DTL_int, this means that the A-sense can be tracked, and the routine branches to block 112 and sets the V_Esc equal to VA_int+AV_delay, i.e., normal tracking. Then the routine identifies the A_Event as an NAS at 114, and exits. Returning to block 110, if the combined value is not greater than or equal to DTL_int, the routine goes to block 116 and compares VA_int+AV_delay+Max_AV_Extension to DTL_int. If this comparison is negative, this means that no tracking can be permitted, and the routine goes to block 120. The ventricular escape interval remains unchanged, and at block 125 the atrial event is identified as an NAB. However, if the comparison at 116 is yes, then V_Esc is set equal to the value of DTL_int. This causes tracking at the maximum rate, resulting in an extended AV-delay. Following this the routine goes block 114 and identifies the atrial event as an NAS.

It is seen that the result of the logic of FIG. 3B is that the VV_interval may be set as DTL_int, the interval corresponding to the upper limit of the physiological range, i.e., the highest rate that can be tracked. Each successive cycle the synchronous VP occurs closer in time to the atrial sense, even though the AV-delay is still extended. This continues for the number of cycles necessary in order for the comparison at block 110 to be yes, at which point normal tracking is resumed.

Referring now to FIG. 4, there is shown a timing diagram where every other cycle involves an NAB-NVS sequence, and alternate cycles involve an NAS-VP sequence. In this situation, the NAB-VP sequences are not counted, and it takes the pacemaker 20 cycles to detect AVB1. (Note that in FIG. 4 only part of the sequence is shown).

Referring now to FIG. 5, there is shown a timing diagram of another form of pacemaker, having an absolute PVARP (which is a form of ANSP), and a relative PVARP. An AS event in the relative PVARP is not tracked, but likewise does not inhibit delivery of an AP. As seen in this diagram, there is one PAC that occurs within the relative PVARP, and the other A senses occur with a constant rate. This sets up a sequence where a VS appears before the V_Esc times out, but with a long AV_interval due to AVB1. If this sequence continues, the problem is the same as in the case of FIG. 1B, i.e., the long AV-delay results in poor synchronized cardiac operation. The pacemaker of this invention may be adapted in a similar style to look for consecutive cycles, or n out of N cycles as here illustrated, such cycles having an AS in the relative PVARP; no other intervening AS; and then a VS. When this sort of sequence is recognized, the pacemaker diagnoses AVB1, and responds so as to regain tracking. As illustrated, after detection of n out of N sequences, the AV delay is initiated at the end of the relative PVARP, so that ventricular pace pulses are delivered at a maximum ventricular rate. As seen in FIG. 5, the timing is such that the P-wave effectively advances forward in the relative PVARP so that the AV-delay steadily decreases until normal synchronized tracking is achieved.

It is thus seen that there is provided a pacemaker with an effective way to diagnose AVB1 or similar conditions, and to respond in such a way as to regain normal synchronous operation. While the invention has been illustrated by the technique of counting NAB-NVS sequences, or sequences of AS in a relative PVARP followed by a ventricular sense, it is within the scope of the invention also to count AS-VS intervals that exceed a certain predetermined, e.g., programmable, maximum value. Note that the technique of counting NAV-NVS sequences is essentially the same and equivalent to counting AS-VS intervals that exceed a certain time period, and both diagnose the AVB1 condition.

What is claimed is:

1. A dual chamber pacemaker system having VP means for generating ventricular pace pulses for delivery to a patient's ventricle, AS means for sensing spontaneous atrial signals, VS means for sensing spontaneous ventricular signals, tracking means for controlling said VP means to track atrial signals by delivering synchronous ventricular pace pulses in timed relation to sensed atrial signals in the absence of spontaneous ventricular signals, and rate limit means for limiting said tracking means to deliver said ventricular pace pulses at a rate within a predetermined rate range, said pacemaker systems further comprising detection means for detecting a sequence of pacemaker cycles wherein at least some atrial signals are sensed at a sensed rate within said rate range while said rate limit means prevents tracking by said tracking means, and tracking restore means responsive to detection of a said sequence for controlling said tracking means to restore tracking of spontaneous atrial signals at a ventricular pace rate within said range.

2. The pacemaker system as described in claim 1, wherein said detection means has means for detecting event pairs characterized by a normal atrial sense which occurs at a rate within said range but which cannot be tracked (NAB), followed by a normal ventricular sense (NVS).

3. The pacemaker system as described in claim 2 wherein said detection means further comprises data storage having stored data for defining said sequence.

4. The pacemaker system as described in claim 3, wherein said data storage comprises storage of a number n corresponding to counted NAB-NVS pairs.

5. The pacemaker system as described in claim 4, wherein said data comprise a number N corresponding to consecutive pacemaker cycles and said detection means has means for detecting a sequence with at least n said pairs within N pacemaker cycles.

6. The pacemaker system as described in claim 1, wherein said detection means has means for detecting a sequence having a plurality of cycles characterized by at least some of said cycles having a spontaneous AS and a spontaneous VS pair, each said AS and VS pair having a delay corresponding to first degree AV block.

7. The pacemaker system as described in claim 1, wherein said tracking means comprises normal AV means for normally timing out a predetermined normal AV-delay, and said tracking restore means comprises means for tracking sensed atrial signals with an extended AV-delay, and means for controlling said VP means to deliver a ventricular pace pulse at said extended AV-delay following the next atrial sense and before a next occurring ventricular sense.

8. The pacemaker system as described in claim 7, wherein said tracking restore means further comprises means for decreasing the AV interval each subsequent cycle until ventricular pace pulses are delivered at said normal AV-delay.

9. The pacemaker as described in claim 1, wherein said tracking restore means comprises means for controlling said VP means to deliver at least one ventricular pace pulse at a rate higher than said sensed rate, and means for gradually decreasing the AV-delay between an atrial sense and a ventricular pace to a normal AV-delay.

10. The pacemaker system as described in claim 1, wherein said tracking restore means has means for restoring tracking at an AV interval within a predetermined range of normal AV values.

11. A dual chamber pacemaker system having VP means for generating ventricular pace pulses for delivery to a patient's ventricle, AS means for sensing spontaneous atrial signals, VS means for sensing spontaneous ventricular signals, tracking means for controlling said VP means to track atrial signals by delivering synchronous ventricular pace pulses in timed relation to sensed atrial signals in the absence of spontaneous ventricular signals, and rate limit means for limiting said tracking means to deliver said ventricular pace pulses at a rate within a predetermined rate range, said pacemaker system further comprising:

detection means for detecting a condition of ongoing first degree AV block without tracking of atrial signals, and tracking restore means responsive to detection of a said condition for restoring normal tracking of atrial signals.

12. The pacemaker system as described in claim 11, wherein said detection means comprises pattern means for detecting a pattern of atrial-ventricular sequences, where each such sequence has an atrial sense that said tracking means cannot track, followed by a ventricular sense.

13. The pacemaker system as described in claim 12, wherein said sequence is an NAB-NVS sequence.

14. The pacemaker system as described in claim 12, wherein said tracking restore means has means for controlling said VP means to deliver a ventricular pace pulse after an extended AV-delay and before the next expected ventricular sense.

15. The pacemaker system as described in claim 12, wherein pattern means comprises means for detecting N consecutive such sequences.

16. The pacemaker system as described in claim 12, wherein said pattern means comprises means for detecting n of N sequences, where n is a number of such sequences and N is a number of consecutive cycles.

17. A dual chamber pacemaker system having VP means for generating ventricular pace pulses for delivery to a patient's ventricle, AS means for sensing spontaneous atrial signals, VS means for sensing spontaneous ventricular signals, tracking means for controlling said VP means to track atrial signals by delivering synchronous ventricular pace pulses in timed relation to sensed atrial signals in the absence of spontaneous ventricular signals, and rate limit means for limiting said tracking means to deliver said ventricular pace pulses at a rate within a predetermined rate range, said pacemaker system further comprising:

detection means for detecting a condition of first degree AV block wherein atrial signals are sensed but not tracked, and wherein each non-tracked atrial signal is followed by a ventricular sense that occurs before delivery of a ventricular pace pulse, and restore means for restoring normal tracking of atrial senses following a detection of first degree AV block by said detection means.

18. The pacemaker system as described in claim 17, wherein said restore means comprises AV means for controlling said VP means to deliver a ventricular pace pulse at an extended AV interval following an atrial sense so as to override a ventricular sense that would otherwise occur before delivery of a ventricular pace pulse.

\* \* \* \* \*